United States Patent [19] [11] 4,405,237
Manuccia et al. [45] Sep. 20, 1983

[54] COHERENT ANTI-STOKES RAMAN DEVICE

[75] Inventors: Thomas J. Manuccia, Silver Spring, Md.; John F. Reintjes, Alexandria, Va.

[73] Assignee: The United States of America as represented by the Secretary of the Navy, Washington, D.C.

[21] Appl. No.: 231,636

[22] Filed: Feb. 4, 1981

[51] Int. Cl.³ .............................................. G01J 3/44
[52] U.S. Cl. .................................................... 356/301
[58] Field of Search ................................ 356/301, 300

[56] References Cited

U.S. PATENT DOCUMENTS 4,195,930 4/1980 Delhaye et al.

OTHER PUBLICATIONS

"Coherent Anti-Stokes Raman Spectroscopy", Klauminzer et al., Opto-Electronics, Jun. 1977, pp. 183-190.
"Puscars: A Method for Suppression of Nonresonant Background", Kamza et al., Optics Letters, vol. 5, #3, 1980.
A Review of the Theory & Application of CARS, Tolles et al, Applied Spectroscopy, vol. 31, No. 4, 1977, pp. 253-271.
Gas Concentration Measurement by Coherent Raman Anti-Stokes Scattering, Regneir et al, paper given at AIAA 6th Fluid & Plasma Dynamics Conference, Palm Springs, CA, Jul. 16-18, 1973, (Paper No. 73-702).

Primary Examiner—F. L. Evans
Assistant Examiner—L. Dietert
Attorney, Agent, or Firm—Robert F. Beers; William T. Ellis

[57] ABSTRACT

A coherent anti-Stokes Raman spectroscopic (CARS) imaging device especially adapted to observe specific molecular groups in living cells. Two laser beam pulses of different wavelengths in the visible or UV spectra and of picosecond duration are used to simultaneously illuminate a sample (e.g., a living cell) containing molecules of the type it is desired to observe. By proper selection of the laser frequencies, the molecules are excited to emit characteristic coherent anti-Stokes radiation which can be imaged through a microscope or other device.

5 Claims, 1 Drawing Figure

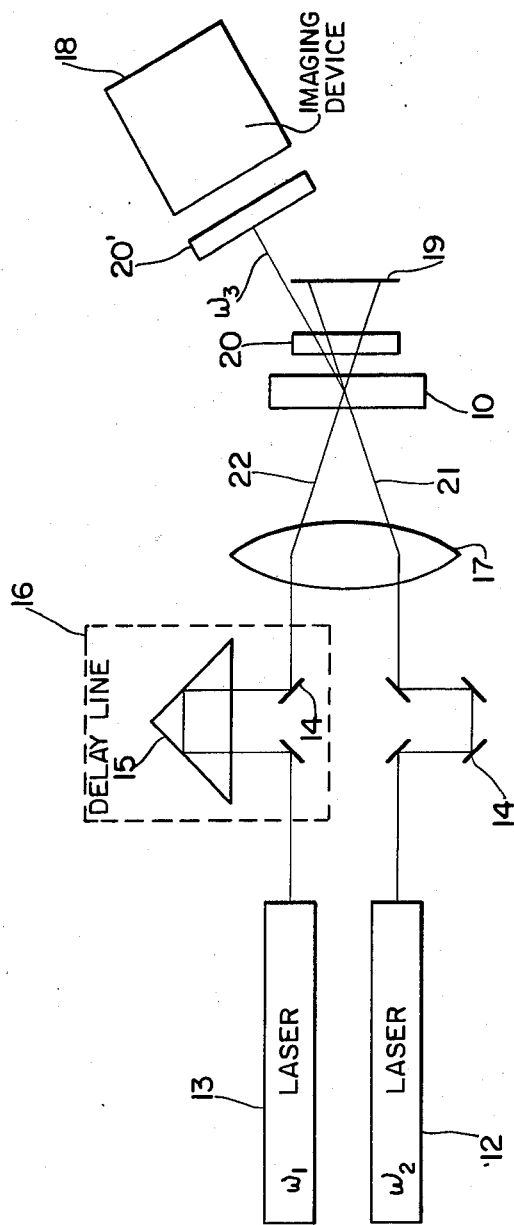

COHERENT ANTI-STOKES RAMAN DEVICE

BACKGROUND OF THE INVENTION

The invention relates to a CARS device and especially to a microscope utilizing coherent anti-Stokes Raman radiation emitted by molecular clusters to image the clusters.

There are five methods currently usable for molecular (not elemental) selective microscopy. Four of the techniques have been used for study of biomolecules. The fifth, a coherent anti-Stokes microscope similar to the type described herein has not been used in the study of molecules. None of the existing techniques have claimed to be capable of distinguishing molecules on the basis of their characteristic infrared energy levels while at the same time providing spatial resolution at the much smaller level characteristic of visible wavelengths.

a. Stains, Fluorescing agents

Generally molecules of biological interest are quite transparent in the visible and are therefore indistinguishable when illuminated with visible radiation. One class of microscopic technique currently in use makes use of chemical preparation of the sample to improve the contrast of molecules of interest by introducing stains or fluorescing agents into the sample. Molecular selectivity is achieved by choosing a stain or fluorescing agent that selectively chemically or physically bonds to specific regions of the sample material, for example, at a particular type of chemical site.

This type of approach has several disadvantages and limitations. The required preparation of the sample can be complex, often requiring much time and effort of a number of workers. Introduction of foreign substances into the sample can alter its function, distorting the information to be obtained from observation of the spatial distribution of the chosen species. It can even alter the physical structure of the sample, yielding complicated artifacts. Suitable stains or fluorescing agents are not available for all samples of interest or for all types of molecular sites, thus restricting the number and type of samples that can be studied in this way. Finally, introduction of fluorescing agents or dyes either can kill living organisms or must be used on fixed samples, preventing study of biological processes in living organisms.

b. Autoradiography

This technique makes use of particles emitted by a sample during radioactive decay to provide an image of molecular distribution within a sample. Selectivity is obtained by introducing characteristic radioactive tracers, e.g., tritium, to the sample before study. The disadvantages of this technique arise from the need for sample preparation and the presence of extremely weak signal levels which often necessitates film exposure time of one week or more on immobilized samples.

c. Spontaneous Raman scattering

The technique makes use of the Raman effect to provide radiation that is shifted in wavelength from the illuminating radiation for obtaining an image of a sample. Molecular selectivity is made on the basis of the existence of characteristic energy levels for each type of molecular species which results in radiation at a differing wavelength for each molecular group.

The shifted radiation lies at longer wavelengths than the illumination wavelength. As a result the Raman Stokes-shifted radiation must be viewed against a background of typically strong fluorescence from the sample which always occurs at longer wavelengths than the illuminating wavelength. Stokes radiation from all molecular species present in the sample is present simultaneously in the scattered light. For most materials these wavelengths lie very close together. As a result molecular discrimination involves imaging through filters that pass a very narrow spectral bandwidth but are simultaneously variable in center wavelength. Usually the only suitable filters are one- or two-grating monochromators. They generally degrade the quality of the image and prevent the full spatial resolution from being achieved. In addition, exposure times are typically long and required illumination levels high restricting biological uses.

d. Infrared microscopes

In this technique the sample is either illuminated with a variable wavelength infrared source or viewed through appropriate filters after broadband infrared illumination. An image of the sample is obtained by imaging the transmitted or scattered infrared radiation. Molecular selectivity is obtained by tuning the wavelength to a vibrational energy level of a selected molecular species in the sample.

The disadvantage of this technique is that the spatial resolution of the image is limited to distances larger than one half the wavelength of the infrared radiation and typically several times the wavelength. This is usually at least 10-20 $\mu$m, which is too large to resolve many structures of biological or chemical interest. In addition, many samples of biological interest are opaque in the infrared due to background absorption from such sources as water. As a result it can be impossible in this technique to obtain images of the spatial distribution of many molecular groups in samples of interest.

e. Coherent Anti-Stokes Microscopy

The sample is illuminated by two laser beams and the image is made by observing the anti-Stokes Raman light. This technique has been applied only to photographing gas distribution in flames but no modification of the technique has been made to permit its application to condensed phase media. Most importantly, no recognition whatsoever has been given to the improved spatial resolution that can be achieved over direct infrared viewing and no attention has been paid to the problems and characteristics of performing microscopy in condensed-phase media.

OBJECTS OF THE INVENTION

An object of the invention is to utilize CARS-type apparatus to image molecular-clusters, especially in living cells, with resolutions comparable to that of optical microscopes.

Another object is to illuminate molecular species with "visible" radiation, as desired, and yet to be able to view them by light whose frequency is in the "visible" spectrum.

A further object is to enlarge the number of molecular species upon which selective microscopy can be accomplished.

A further object is to make optimum use of the available laser energy in a CARS imaging device without excessive sample heating or loss of contrast.

Yet another object is to obtain molecular selectivity based on IR energy levels and yet to view the molecules by light whose frequency is in the visible spectrum.

Yet another object is to view biological processes in living organisms on a subcellular basis.

Other objects, advantages and novel features of the present invention will become apparent from the following detailed description of the invention when considered in conjunction with the accompanying drawing.

DETAILED DESCRIPTION OF THE INVENTION

A schematic illustration of a typical embodiment of apparatus which can be used to implement the invention is shown in the figure. A sample 10 containing molecules which it is desired to image is illuminated by two beams 21 and 22 from lasers 12 and 13, respectively. The beams are of different frequencies, $\omega_1$, and $\omega_2$. The beams may be derived from separate lasers or from a single laser operating at different wavelengths. Preferably, the lasers are pulsed to produce picosecond output pulses. The duration of the optimal pulses in the shorter-wavelength laser beam should be of the order of the dephasing time (inverse linewidth) of the vibrational energy level (Raman-active level) of the molecules being imaged. Typical dephasing times are on the order of several picoseconds or less. The duration of the pulses in the longer-wavelength beam can be of the same duration or longer, but not longer than that required to ensure reliable synchronization of the pulses in the two beams, typically on the order of 10 picoseconds. The pulses in the two beams are synchronized by adjusting the separation of the mirrors 14 and roof top mirror 15 in the delay line 16, thereby adjusting the path length of one laser beam relative to the other.

The laser beams strike a lens 17 on parallel paths and are adjusted to cross the sample 10 at the focus of the lens. The angle of crossing of the beams may be adjusted to satisfy the phase-matching requirements of CARS scattering by adjusting the separation of the beams at the lens 17 but this is not necessary in all embodiments of the invention. The angle depends on the dispersion of the index of refraction and the length of the medium. In selecting the optimal angle, it is endeavored to maintain the coherence of the interaction.

Molecular selectivity, i.e., selection of the molecule it is desired to observe, is obtained by adjusting the wavelength of the tunable laser so that the difference in photon energy, $\Delta E$, is equal to the spacing from the ground level of the Raman-active energy level in the selected molecular species to be imaged. The Raman-active vibrational level is typically at an infra-red energy level. The phonton energy difference $$\Delta E = hc\left(\frac{1}{\lambda_1} - \frac{1}{\lambda_2}\right),$$

where h is Planck's constant, c is the speed of light, $\lambda_1$ is the wavelength of one laser beam and $\lambda_2$ is the wavelength of the other. (The photon energy relation can also be expressed in terms of the frequency of the vibrational energy level and the frequencies of the illuminating laser beams, viz., $\omega_v = \omega_1 - \omega_2$. The frequency of the anti-Stokes Raman radiation emitted by the molecular species which is thus excited is $\omega_3 = 2\omega_1 - \omega_2$.

Through the coherent anti-Stokes Raman process, radiation $\omega_3$ is generated at a shorter wavelength than that of either of the two illuminating sources. This anti-Stokes radiation is viewed by means of an appropriate imaging device 18, such as a microscope, television camera, photographic emulsion, etc., to obtain an image of the distribution of the selected molecular species within the sample. Unshifted radiation from the illumination lasers is prevented from reaching the detector 18 by screens 19 and filters 20 and 20'.

It is desirable that an anti-Stokes radiation frequency $\omega_3$ in the visible or UV bands be selected for the imaging step since better resolution is obtainable in these bands than in the infra-red (IR). In blue light, the limit of resolution is about $\frac{1}{2}\mu$ and in UV, about $\frac{1}{4}\mu$.

The invention makes use of anti-Stokes radiation to obtain an image of the distribution of selected, naturally occurring molecular species using characteristic infra-red energy levels for molecular selectivity, but with improved spatial resolution over what has previously been available with condensed-phase-media molecules.

The invention overcomes many of the limitations of the staining and fluorescing agents and of radioactive tracer agents by eliminating the need for introducing foreign agents into the sample. This increases the number of materials on which molecular species-selective microscopy can be performed. Most importantly it also enlarges the capability for the first time of viewing biological processes in living organisms on a subcellular basis.

The use of anti-Stokes Raman radiation allows improved spatial resolution over that which could be obtained with IR radiation tuned to the same IR vibrational transition, overcoming the limitation on resolution imposed by IR microscopy.

The use of anti-Stokes Raman radiation permits the suppression of confusion occurring from sample fluorescence because the anti-Stokes radiation is at shorter wavelengths than the illumination sources in a spectral region with no sample fluorescence, which is one of the main difficulties encountered when spontaneous Raman scattering is employed for imaging.

The use of the wavelength difference of the illumination sources for molecular selectivity allows the use of relatively broadband spectral filters at the detector as these filters have only to discriminate against the illumination wavelengths rather than against unwanted Raman-shifted light. As a result, the spectrometers needed in the spontaneous Raman microscope can be eliminated and the spatial resolution can be improved.

The use of picosecond pulses allows the duration of the light source to be matched to the lifetimes of the excitation in condensed media. Optimum use is thus made of the available laser energy without excessive sample heating or loss of contrast due to delay of the infra-red vibration or diffusion of the excitation out of resolution element. These points were not important and were not considered in the CARS device which has been used to photograph molecular distribution in gases.

Some alternatives for the equipment described herein are listed below:

1. Each of the two lasers can be tunable. This allows a wider range of molecular energy levels and materials to be studied.

2. The lasers can be in the near ultraviolet. Although visible-band lasers are also set forth herein, the only restriction in their wavelengths is that the samples be transparent at the anti-Stokes wavelength. Thus, any combination of wavelengths for which the anti-Stokes wavelength is above about 300 nm can be used for the pump lasers.

3. Deuterium can be substituted for hydrogen in material introduced into a biological sample. Such a substitution is minor compared to the chemical preparation of conventional microscope samples and can allow processes such as uptake and distribution of nutrients, drugs, toxins, etc., to be studied.

4. The lasers can be focused to dimensions of the order of a wavelength of light. In this arrangement, spatial resolution can be defined by the illuminating lasers and a full image of the sample is obtained by scanning the pair of beams over the sample. This technique makes optimum use of pump intensity which minimizes overall sample heating.

5. The two beams can be crossed without focusing. Such a geometry is useful if there is enough laser power available and can give a relatively wide field of view with scattering available from all parts of the sample illuminated simultaneously by the lasers.

6. If the sample, or the volume of the sample occupied by the selected molecule, is sufficiently thin, the angle between the illuminating laser beams can be very small or zero.

Obviously, many modifications and variations of the present invention are possible in light of the above teachings. It is therefore to be understood that, within the scope of the appended claims, the invention may be practiced otherwise than as specifically described.

What is claimed is:

1. A molecular selective microscopy method for microscopically imaging selected molecular species in a condensed-phase medium comprising the steps of:

illuminating a sample containing the molecules of the selected species with a pair of pulsed laser beams of different frequencies, $\omega_1$ and $\omega_2$, and corresponding wavelengths $\lambda_1$ and $\lambda_2$, respectively, where the difference in photon energy between the wavelengths is $$\Delta E = hc\left(\frac{1}{\lambda_1} - \frac{1}{\lambda_2}\right),$$

$\Delta E$ being equal to the spacing from ground level of a desired Raman-active energy level in the selected molecular species, the pulse durations of said laser beams being of the order of picoseconds, each pair of associated pulses of the two beams being simultaneous over at least a portion of the time duration of one of the pulses; and microscopically imaging the anti-Stokes Raman emission from the molecular species which occurs at the frequency $\omega_3 = 2\omega_1 - \omega_2$, the frequencies $\omega_1$ and $\omega_2$ being selected so that $\omega_3$ is in the visible or UV light bands, and $\omega_1$ and $\omega_2$ also being in the "visible" light bands.

2. A method as in claim 1, wherein:

the duration of the pulses from one of said laser beams lies in the 1-10 picosecond range.

3. A CARS imaging device for microscopically imaging a specific molecular species in a condensed-phase medium sample:

means for generating pairs of pulses from two laser beams of different frequencies, $\omega_1$ and $\omega_2$, and focusing each associated pair on said sample, the pulse durations being of the order of picoseconds, and each associated pair of pulses being simultaneous over at least a portion of the time duration of one of the pulses, the laser frequencies being selected so that the frequency $\omega_v = \omega_1 - \omega_2$ is the frequency of an anti-Stokes vibrational level of said specific molecular species, said anti-Stokes vibration of the molecular species emitting radiation of frequency $\omega_3 = 2\omega_1 - \omega_2$, where $\omega_1$, $\omega_2$ and $\omega_3$ are in the "visible" light spectrum; and microscope means for imaging the emitted anti-Stokes radiation from the molecular species.

4. A CARS imaging device as in claim 3, wherein:

the duration of at least one of the pulses in any pair lies in the 1-10 picosecond range.

5. A CARS imaging device as in claim 3, wherein:

said means for generating laser beams is tunable so that at least one of said laser beams is adjustable in frequency.

* * * * *